United States Patent
Qiao et al.

(10) Patent No.: US 11,209,468 B2
(45) Date of Patent: Dec. 28, 2021

(54) APPARATUS AND METHOD FOR DETECTING OBJECT FEATURES

(71) Applicant: Silergy Semiconductor Technology (Hangzhou) LTD, Hangzhou (CN)

(72) Inventors: Junjie Qiao, Hangzhou (CN); Yanji Chen, Hangzhou (CN)

(73) Assignee: Silergy Semiconductor Technology (Hangzhou) LTD, Hangzhou (CN)

( * ) Notice: Subject to any disclaimer, the term of this patent is extended or adjusted under 35 U.S.C. 154(b) by 425 days.

(21) Appl. No.: 15/978,307

(22) Filed: May 14, 2018

(65) Prior Publication Data

US 2018/0335457 A1 Nov. 22, 2018

(30) Foreign Application Priority Data

May 19, 2017 (CN) .......................... 201710359459.4

(51) Int. Cl.
| | |
|---|---|
| *G01R 23/167* | (2006.01) |
| *A61B 5/08* | (2006.01) |
| *H03M 1/66* | (2006.01) |
| *H03M 1/12* | (2006.01) |
| *A61B 5/024* | (2006.01) |

(Continued)

(52) U.S. Cl.
CPC ........ *G01R 23/167* (2013.01); *A61B 5/02444* (2013.01); *A61B 5/0507* (2013.01); *A61B 5/0816* (2013.01); *A61B 5/1102* (2013.01); *A61B 5/1135* (2013.01); *A61B 5/725* (2013.01); *H03M 1/12* (2013.01); *H03M 1/66* (2013.01)

(58) Field of Classification Search
CPC .... G01N 2291/017; G01N 2291/02483; A61B 5/0507; A61B 5/0816; A61B 5/024; A61B 5/0205; A61B 5/05
See application file for complete search history.

(56) References Cited

U.S. PATENT DOCUMENTS 5,055,850 A * 10/1991 Lamper .................. G01S 13/90
342/201
8,270,671 B1 9/2012 Medasani et al.
(Continued)

FOREIGN PATENT DOCUMENTS

| CN | 201114160 Y | 9/2008 |
|---|---|---|
| CN | 101458326 A | 6/2009 |

(Continued)

OTHER PUBLICATIONS

Yamana, A Sensor for Monitoring Pulse Rate, Respiration Rhythm, and Body Movement in Bed, 33rd Annual International Conference of the IEEE EMBS Boston, Massachusetts USA, Aug. 30-Sep. 3 (Year: 2011).*

(Continued)

*Primary Examiner* — Michael J Dalbo

(57) ABSTRACT

An apparatus for detecting object features can include: a probe signal transmitter configured to load a digital intermediate frequency signal onto a carrier signal, and to transmit a loaded signal outwards; an echo signal receiver configured to receive an echo signal, and to extract an object feature signal by performing respective down conversions on a quadrature signal of the carrier signal and a quadrature signal of the digital intermediate frequency signal; and a signal processor configured to identify object features according to the object feature signal.

20 Claims, 15 Drawing Sheets

(51) Int. Cl.
*A61B 5/0507* (2021.01)
*A61B 5/00* (2006.01)
*A61B 5/11* (2006.01)
*A61B 5/113* (2006.01)

(56) References Cited

U.S. PATENT DOCUMENTS

| | | | | |
|---|---|---|---|---|
| 2004/0141546 | A1* | 7/2004 | Nakamura | H04B 1/7174 375/130 |
| 2004/0172438 | A1* | 9/2004 | Gunzelmann | H03C 3/40 708/607 |
| 2008/0074307 | A1* | 3/2008 | Boric-Lubecke | G01S 13/56 342/28 |
| 2008/0238757 | A1* | 10/2008 | Lin | G01S 13/38 342/22 |
| 2009/0036760 | A1* | 2/2009 | Hayter | A61B 5/7221 600/316 |
| 2010/0073222 | A1* | 3/2010 | Mitomo | G01S 13/345 342/175 |
| 2013/0034193 | A1* | 2/2013 | Du | H03C 1/00 375/340 |
| 2013/0142287 | A1* | 6/2013 | Kravets | H04B 1/1027 375/340 |
| 2013/0324855 | A1* | 12/2013 | Lisogurski | A61B 5/0402 600/476 |
| 2015/0317816 | A1 | 11/2015 | Bendall et al. | |
| 2015/0325013 | A1 | 11/2015 | Patnaik | |
| 2017/0105659 | A1* | 4/2017 | Kiaei | A61B 5/1102 |

FOREIGN PATENT DOCUMENTS

| | | |
|---|---|---|
| CN | 104434059 A | 3/2015 |
| CN | 205899013 U | 1/2017 |

OTHER PUBLICATIONS

Chuan Lin, Research on the Key Technologies about Wide-band HF Data Transmission System, Chinese Master's Theses Full-text Database, I136-544, Nov. 15, 2014.

* cited by examiner

APPARATUS AND METHOD FOR DETECTING OBJECT FEATURES

RELATED APPLICATIONS

This application claims the benefit of Chinese Patent Application No. 201710359459.4, filed on May 19, 2017, which is incorporated herein by reference in its entirety.

FIELD OF THE INVENTION

The present invention generally relates to wireless detection technology, and more particularly detection of object features.

BACKGROUND

Existing technology for detecting an active object is generally implemented with a Doppler radar. FIG. 1 is a block diagram of an example system for detecting object features. This example system for detecting the object features transmits a radar signal to the object through microwave transceiver 91, and receives an echo signal reflected by the object. A low frequency signal may be generated by mixing the echo signal with the radar signal, and the object features can be obtained by detecting the frequency of the amplified low frequency signal through digital signal processor (DSP) or threshold judgment circuit 92. However, this approach for detecting the object features may be susceptible to external clutter interference, and may have relatively poor accuracy.

DETAILED DESCRIPTION

Reference may now be made in detail to particular embodiments of the invention, examples of which are illustrated in the accompanying drawings. While the invention may be described in conjunction with the preferred embodiments, it may be understood that they are not intended to limit the invention to these embodiments. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it may be readily apparent to one skilled in the art that the present invention may be practiced without these specific details. In other instances, well-known methods, procedures, processes, components, structures, and circuits have not been described in detail so as not to unnecessarily obscure aspects of the present invention.

In one embodiment, an apparatus for detecting object features can include: (i) a probe signal transmitter configured to load a digital intermediate frequency signal onto a carrier signal, and to transmit a loaded signal outwards; (ii) an echo signal receiver configured to receive an echo signal, and to extract an object feature signal by performing respective down conversions on a quadrature signal of the carrier signal and a quadrature signal of the digital intermediate frequency signal; and (iii) a signal processor configured to identify object features according to the object feature signal.

Figure 1:
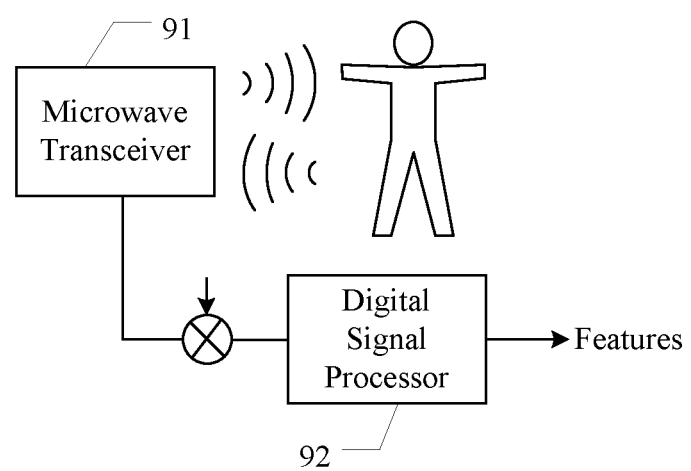
FIG. 1 is a block diagram of an example system for detecting object features.
Figure 2:
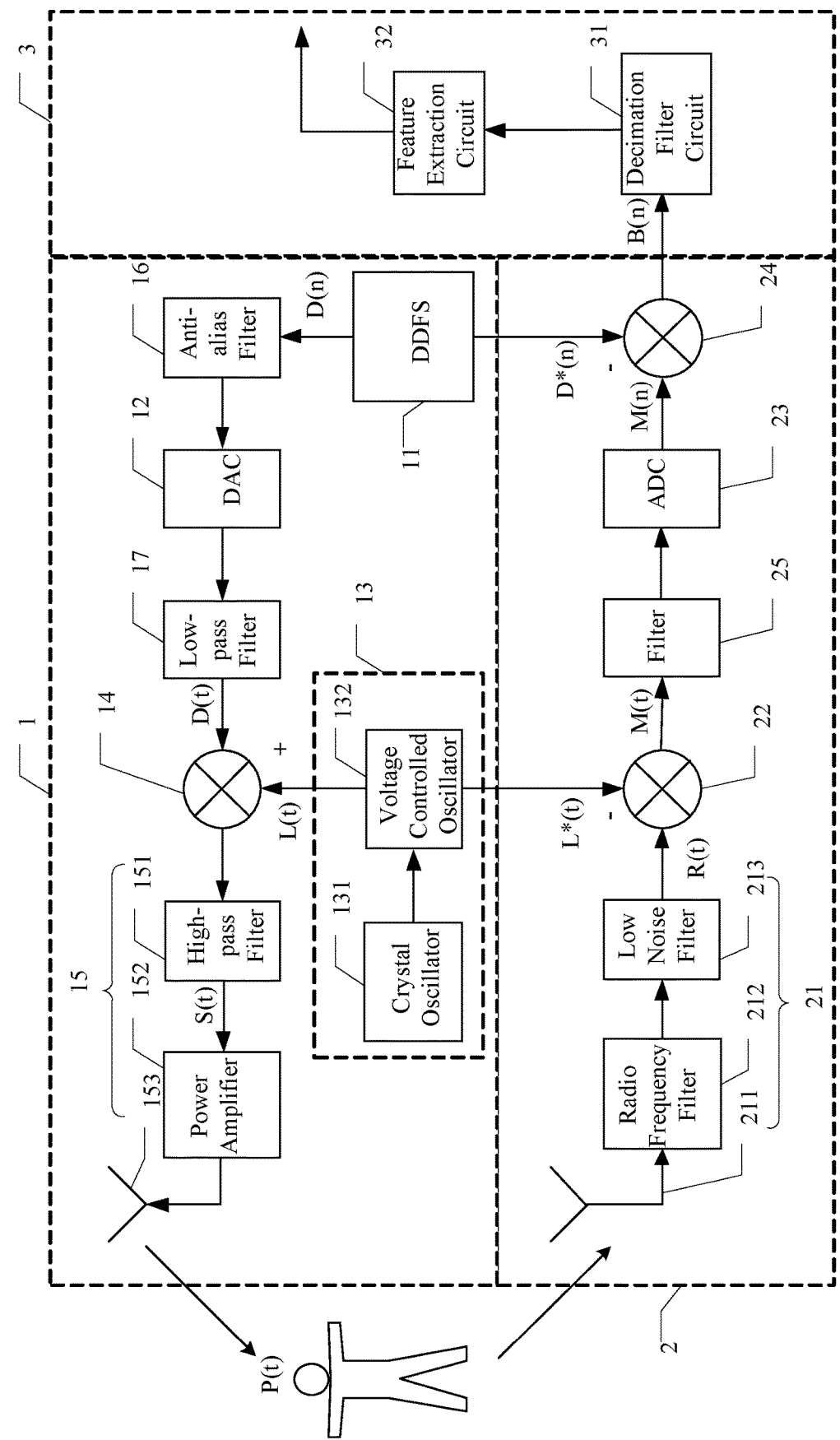
FIG. 2 is a block diagram of an example apparatus for detecting object features, in accordance with embodiments of the present invention.

Referring now to FIG. 2, shown is a block diagram of an example apparatus for detecting object features, in accordance with embodiments of the present invention. This particular example apparatus for detecting object features can include probe signal transmitting terminal 1, echo signal receiving terminal 2, and signal processor 3. Probe signal transmitting terminal 1 can load predetermined intermediate frequency signal D(n) onto carrier signal L(t) of a predetermined frequency, and may transmit the loaded signal outwards. Echo signal receiving terminal 2 can receive an echo signal in a predetermined frequency band, and may extract object feature signal B(n) by respectively performing down conversions on a quadrature signal of carrier signal L(t) and a quadrature signal of digital intermediate frequency signal D(n).

The down conversion may generally utilize the quadrature signal of a corresponding signal. The quadrature signal may be obtained by processing original carrier signal L(t) and digital intermediate frequency signal D(n), or may be obtained directly by the circuit from which carrier signal L(t) and digital intermediate frequency signal D(n) are generated. Signal processor 3 can identify the object features according to the object feature signal. Carrier signal L(t) may be a radio frequency carrier signal with a predetermined frequency, and the echo signal may be a radio frequency signal.

For example, probe signal transmitting terminal 1 can include direct digital frequency synthesizer (DDFS) 11, digital-to-analog converter (DAC) 12, carrier wave generator 13, mixer 14, and transmitting circuit 15. DDFS 11 can generate digital intermediate frequency signal D(n). DDFS 11 may be a new frequency synthesizer that directly synthesizes required waveforms from a phase concept. As compared with a conventional frequency synthesizer, the DDFS may have advantages of low cost, low power, high resolution, and fast switching time. DAC 12 can convert digital intermediate frequency signal D(n) to analog intermediate frequency signal D(t). Carrier wave generator 13 may generate carrier signal L(t).

Carrier wave generator 13 may include crystal oscillator 131 and voltage controlled oscillator (VCO) 132. VCO 132 can convert a fixed frequency signal generated by crystal oscillator 131 to carrier signal L(t) corresponding to the control voltage, and may output carrier signal L(t). Mixer 14 can load analog intermediate frequency signal D(t) onto carrier signal L(t). Transmitting circuit 15 can transmit the mixed radio frequency signal. Transmitting circuit 15 may include high-pass filter 151, power amplifier 152, and antenna 153. High-pass filter 151 can remove the externally introduced low frequency interfere interference, in order to improve signal quality.

For example, probe signal transmitting terminal 1 may also include anti-alias filter 16 and low-pass filter 17. Anti-alias filter 16 can be provided between DDFS 11 and DAC 12, for anti-alias filtering digital intermediate frequency signal D(n). Frequency aliasing is a phenomenon whereby high and low frequency components are aliased due to a change in the frequency spectrum of a sampled signal. When the sampling frequency is not high enough, the sampled point may represent not only the sample value of the low frequency component in the sampled signal, but also the sample value of the high frequency component.

When the sampled signal is reconstructed, the high frequency component can be replaced by the low frequency component, and the two waveforms may be completely overlapped, which can result in a serious distortion. Anti-alias filter 16 may actually be a low-pass filter having a function to reduce the aliased frequency components in the output level. In this way, frequency aliasing can be prevented during digital-to-analog conversion, and the accuracy of the apparatus for detecting the object features can be further improved. Low-pass filter 17 may be provided between DAC 12 and mixer 14, for performing low-pass filtering on the signal obtained through digital-to-analog conversion, in order to remove the high frequency noises.

Echo signal receiving terminal 2 can include receiving circuit 21, down converter 22, analog-to-digital converter (ADC) 23, and down converter 24. Receiving circuit 21 can receive the radio frequency signal in a predetermined receiving frequency band. The receiving frequency band may be determined according to the carrier signal, and can be located in the vicinity of the radio frequency carrier frequency. Receiving circuit 21 may include receiving antenna 211, radio frequency filter 212, and low noise amplifier 213. Receiving antenna 211 can resonantly convert the electromagnetic waves in the space into the radio frequency signal in a predetermined frequency band. Radio frequency filter 212 can remove noise in the received radio frequency signal.

Low noise amplifier 213 can amplify the weak radio frequency signal, and may generate received radio frequency signal R(t). Down converter 22 can perform down conversion on received radio frequency signal R(t) according to quadrature signal L*(t) of carrier signal L(t), in order to obtain analog intermediate frequency receiving signal M(t). ADC 23 can convert analog intermediate frequency receiving signal M(t) to digital intermediate frequency receiving signal M(n). Down converter 24 can perform digital down conversion on digital intermediate frequency receiving signal M(n) according to quadrature signal D*(n) of digital intermediate frequency signal D(n), in order to extract object feature signal B(n).

For example, filter 25 may be provided between down converter 22 and ADC 23, in order to filter analog intermediate frequency signal M(t) obtained by first down conversion before performing the analog-to-digital conversion, so as to improve the system accuracy. Signal processor 3 may include decimation filter circuit 31 and feature extraction circuit 32. Decimation filter circuit 31 can filter object feature signal B(n), so as to reduce the computational complexity of subsequent feature extraction. Feature extraction circuit 32 can identify features in object feature signal B(n) based on a predetermined feature identify algorithm. Decimation filter circuit 31 may be implemented with an application specific integrated circuit (ASIC), or with a programmable device together with feature extraction circuit/circuit 32.

In one embodiment, a method of detecting object features can include: (i) loading a predetermined digital intermediate frequency signal onto a carrier signal with a predetermined frequency, and transmitting a loaded signal outwards; (ii) receiving an echo signal in a predetermined receiving frequency band, and extracting an object feature signal by performing respective down conversions on a quadrature signal of the carrier signal and a quadrature signal of the digital intermediate frequency signal; and (iii) identifying object features according to the object feature signal.

Figure 3:
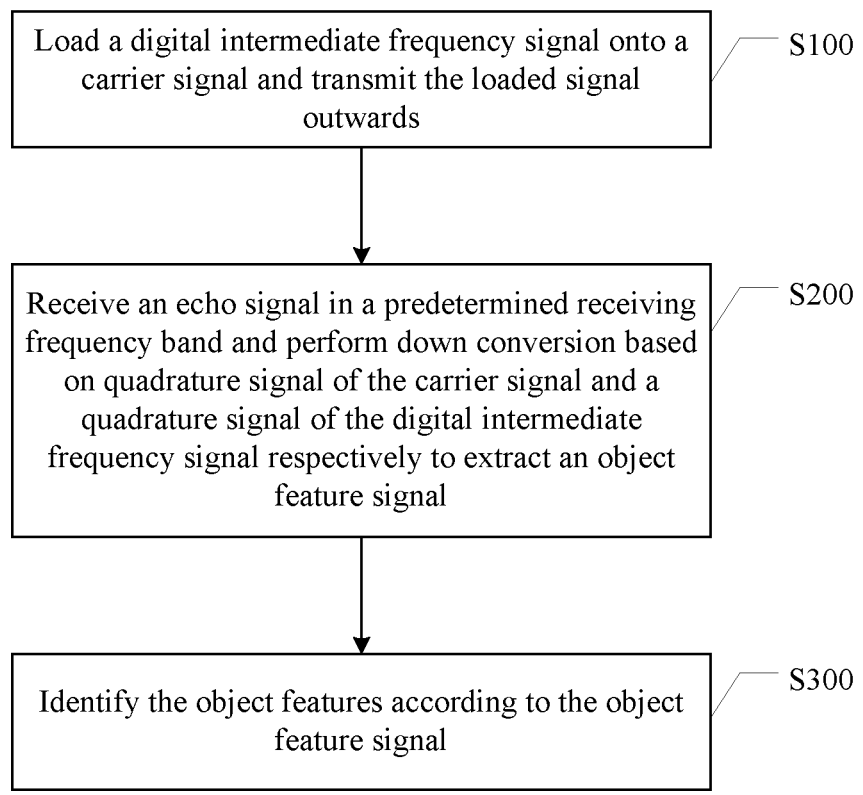
FIG. 3 is a flow diagram of an example method of detecting object features, in accordance with embodiments of the present invention.

Referring now to FIG. 3, shown is a flow diagram of an example method of detecting object features, in accordance with embodiments of the present invention. The following describes the principles of the apparatus and method for detecting object features in particular embodiments in conjunction with FIGS. 3-7. The apparatus for detecting object features can perform the object feature detection according to the following steps. At S100, a predetermined digital intermediate frequency signal D(n) can be loaded onto carrier signal L(t) with a predetermined frequency and transmitting the loaded signal outwards.

Figure 4:
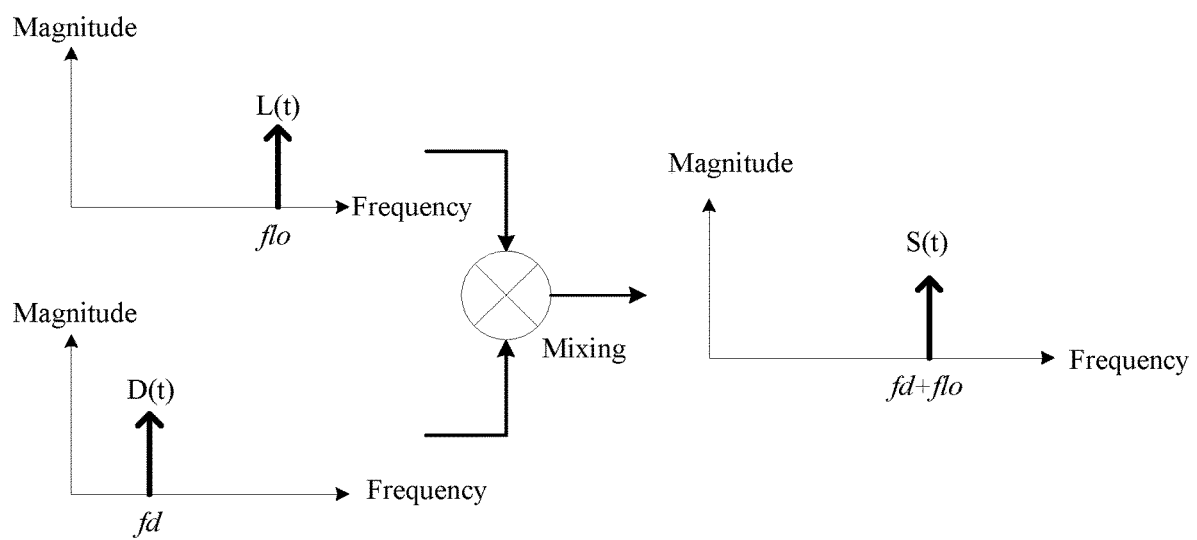
FIG. 4 is a spectrum diagram of an example probe signal transmitted, in accordance with embodiments of the present invention.

Referring now to FIG. 4, shown is a spectrum diagram of an example probe signal transmitted, in accordance with embodiments of the present invention. In this particular example, the frequency of the digital intermediate frequency signal is fd, and its ideal frequency spectrum is an impulse signal at frequency fd. In addition, the frequency of carrier signal is flo, and its ideal frequency spectrum is an impulse signal at frequency flo. For example, the frequency band of the carrier signal may be 2.4 GHz or 5.8 GHz that can be customized by manufacturers. A periodic signal with frequency of flo+fd may be obtained by mixing the analog intermediate frequency signal and the carrier signal corresponding to the digital intermediate frequency signal. The periodic signal is probe signal S(t) transmitted by probe signal transmitting terminal 1, and its ideal frequency spectrum can be an impulse signal at frequency flo+fd. For example, probe signal S(t) is a signal with a relative narrow bandwidth and a center frequency at flo+fd.

Step S100 of FIG. 3 may also include generating digital intermediate frequency signal D(n), where D(n) satisfies: $D(n)=e^{j2\pi fdn}$. Step S100 may also include converting digital intermediate frequency signal D(n) to an analog intermediate frequency signal D(t), where D(t) satisfies: $D(t)=e^{j2\pi fdt}$. For example, before digital-to-analog conversion is performed, anti-alias filtering may be performed through anti-alias filter 16, in order to avoid frequency aliasing during the digital-to-analog conversion. Step S100 of FIG. 3 may also include generating carrier signal L(t), where L(t) satisfies: $L(t)=e^{j2\pi flot}$. Step S100 may also include loading analog intermediate frequency signal D(t) onto carrier signal L(t), in order to obtain mixed radio frequency signal S(t). Step S100 may also include transmitting mixed radio frequency signal S(t). For example, high-pass filter may be performed on radio frequency signal S(t) prior to transmission, in order to remove noise.

In FIG. 3, at S200, radio frequency signal R(t) can be received in a predetermined receiving frequency band, and object feature signal B(n) may be extracted by respectively performing down conversion based on quadrature signal L*(t) of the carrier signal, and quadrature signal D*(n) of the digital intermediate frequency signal. Quadrature signal L*(t) of the carrier signal may be directly generated by carrier wave generator 13. Quadrature signal D*(n) of the digital intermediate frequency signal may be generated by DDFS 11. Step S200 may also include receiving an echo signal in a predetermined receiving frequency band.

Figure 5:
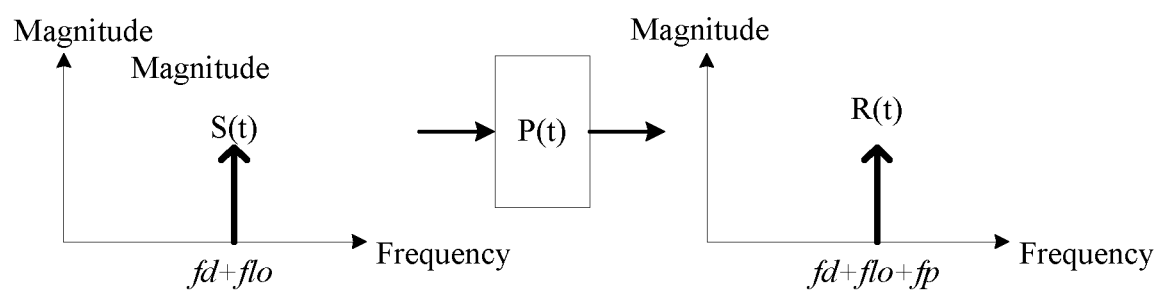
FIG. 5 is a spectrum diagram of an example echo signal modulated by a human body, in accordance with embodiments of the present invention.

Referring now to FIG. 5, shown is a spectrum diagram of an example echo signal modulated by a human body, in accordance with embodiments of the present invention. In this example, after radio frequency signal S(t) as the probe signal is transmitted to the outside, if there is an object in the signal propagation path, echo signal R(t) can be formed by reflecting and scattering the probe signal. Echo signal R(t) may contain the object motion information and other information P(t) characterizing a change of the object, which can cause echo signal R(t) to contain other frequency components outside the frequency band of the probe signal. Therefore, the reflection and scattering of the probe signal by the object can be equivalent to modulation on the probe signal by the object [feature function P(t)], so as to obtain echo signal R(t). The feature function P(t) of a corresponding object may satisfy: $P(t)=e^{j2\pi fpt}$. Echo signal R(t) may satisfy formula (1) below.

$$R(t)=S(t)*P(t)=e^{j2\pi(flo+fd)t}*e^{j2\pi fpt}=e^{j2\pi(flo+fd+fp)t} \quad (1)$$

For example, when the object is a moving object, echo signal R(t) can mainly contain the motion information of the moving object, and when the object is a stationary object, echo signal R(t) can mainly contain the respiratory and heartbeat information of the stationary object. Step S200 in FIG. 3 can also include performing down conversion on the received echo signal according to quadrature signal L*(t) of the carrier signal, and obtaining analog intermediate frequency signal M(t). The down conversion process can be identified by the following formula, i.e., M(t) satisfies formula (2) as below.

$$M(t)=P(t)*L*(t)=e^{j2\pi(flo+fd+fp)t}*e^{-j2\pi flot}=e^{j2\pi(fd+fp)t} \quad (2)$$

Figure 6:
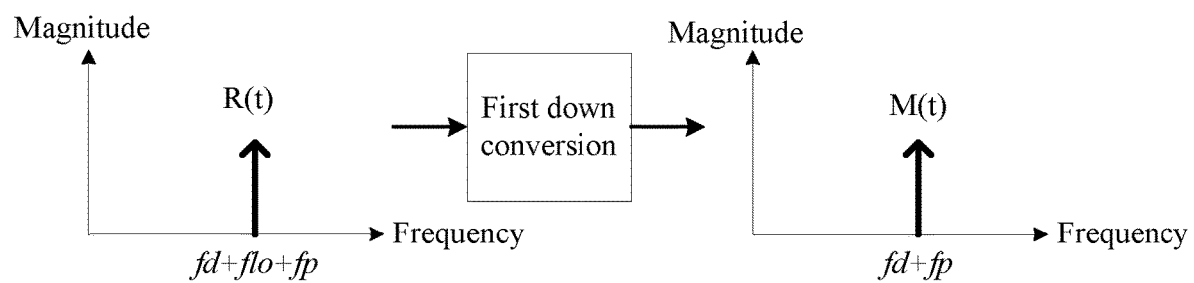
FIG. 6 is a spectrum diagram of an example performing a first down conversion on a received signal, in accordance with embodiments of the present invention.

Referring now to FIG. 6, shown is a spectrum diagram of an example performing a first down conversion on a received signal, in accordance with embodiments of the present invention. In this example, the frequency spectrum of receiving signal R(t) may be moved from frequency flo+fd+fp down to frequency fd+fp. Step S200 of FIG. 3 can also include converting analog intermediate frequency receiving signal M(t) to digital intermediate frequency receiving signal M(n). Digital intermediate frequency receiving signal M(n) may satisfy: $M(n)=e^{j2\pi(fd+fp)n}$. For example, filtering can be performed before analog-to-digital conversion, so as to make preparation for the analog-to-digital conversion. Step S200 of FIG. 3 can also include performing digital down conversion on digital intermediate frequency receiving signal M(n) according to quadrature signal D*(n) of the digital intermediate frequency signal, and obtaining object feature signal B(n). Object feature signal B(n) can satisfy formula (3) below.

$$B(n)=M(n)*D*(n)=e^{j2\pi(fd+fp)n}*e^{-j2\pi fdn}=e^{j2\pi fpn} \quad (3)$$

Figure 7:
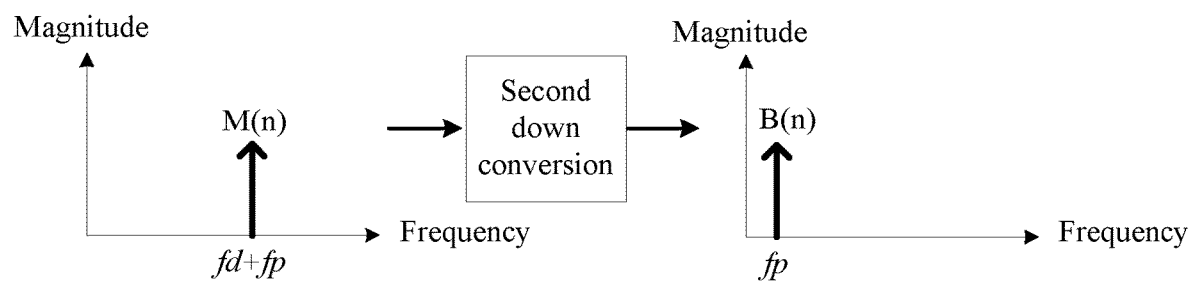
FIG. 7 is a spectrum diagram of an example performing a second down conversion on a received signal, in accordance with embodiments of the present invention.

Referring now to FIG. 7, shown is a spectrum diagram of an example performing a second down conversion on a received signal, in accordance with embodiments of the present invention. In this example, after the second down conversion, the digital signal corresponding to original object feature function P(t), e.g., object feature signal B(n), can be extracted, and object feature signal B(n) can contain feature information of the object (e.g., motion information, heartbeat information, respiratory information, etc.).

At step S300 of FIG. 3, the object features can be identified according to the object feature signal B(n). Here, the object feature signal may be analyzed in the frequency domain, and the object features can be obtained by analyzing the object feature signal at frequencies where different features may appear. For example, when the object is a moving object, the object features can include a moving speed, a respiratory frequency, and a heart rate. The Doppler shift produced by the motion of the object is $2v/\lambda$, where v is the moving speed, and $\lambda$ is the wavelength of the radio frequency signal. Therefore, the information at the frequency point $2v/\lambda$ of object feature signal B(n) is the information that represents the moving speed.

The scope of the moving speed can be obtained according to the limit speed of the target object. Also, for a human body, the respiratory frequency is typically in the range of 0.13-0.40 Hz, and the heartbeat frequency is typically in the range of 0.83-3.3 Hz. It can be seen that the above three frequency ranges do not coincide with each other. Therefore, in the corresponding frequency range, the magnitude or change of object feature signal B(n) may represent the conditions of respiration and heartbeat. That is to say, signal processor 3 can detect information of the object feature signal in a first frequency band, a second frequency band, and a third frequency band, in order to obtain the moving speed, the respiratory frequency, and the heart rate of the moving object. For example, the first frequency band can correspond to the range of the moving speed, the second frequency band can correspond to the range of the respiratory frequency, and the third frequency band can correspond to the range of the heart rate.

In an alternative embodiment, signal processor 3 may determine whether the detected object is a moving object or whether a moving object exists in the detection range based on whether the object feature signal contains the information of the respiratory frequency, the heart rate, and the moving speed. That is to say, signal processor 3 can determine the presence of a moving object in the detection range by detecting the object feature signal as to whether a predetermined signal exists in the first, second, and/or third frequency band. For example, the first frequency band can correspond to the range of the moving speed, the second frequency band can correspond to the range of the respiratory frequency, and the third frequency band can correspond to the range of the heart rate.

Figure 8:
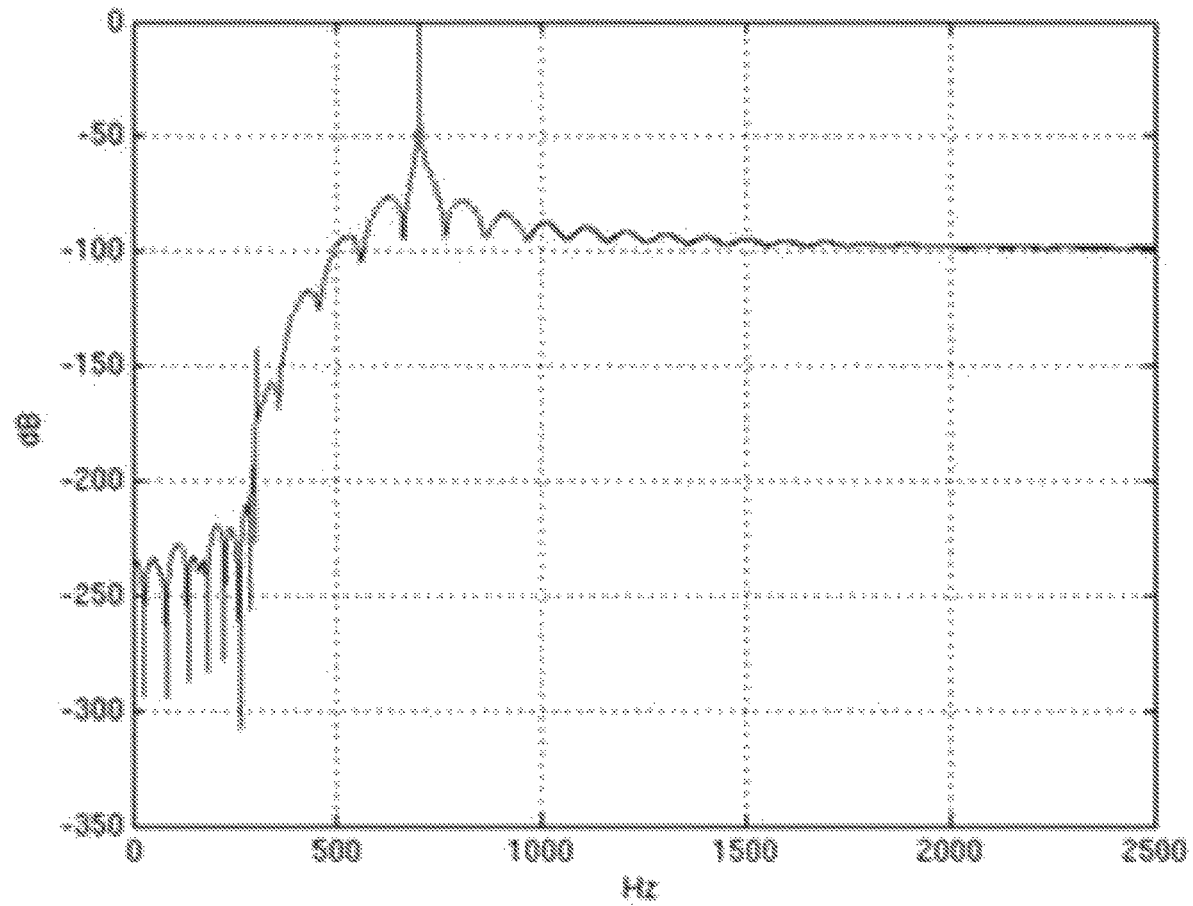
FIG. 8 is a simulated spectrum diagram of an example radio signal transmitted, in accordance with embodiments of the present invention.

Referring now to FIG. 8, shown is a simulated spectrum diagram of an example radio signal transmitted, in accordance with embodiments of the present invention. In this example, since the characteristics of the low-frequency component and the high-frequency component are the same during the simulation, for ease of presentation, the frequency of the carrier signal is selected to be 500 Hz and the frequency of the intermediate frequency is 200 Hz. The above two frequencies are both much larger than the frequency of the human feature, thus the spectral distribution state at higher frequency can be approximately represented equivalently. As shown, the echo signal with a frequency of 700 Hz may be obtained by mixing the carrier signal and the analog intermediate frequency signal at the probe signal transmitting terminal.

Figure 9:
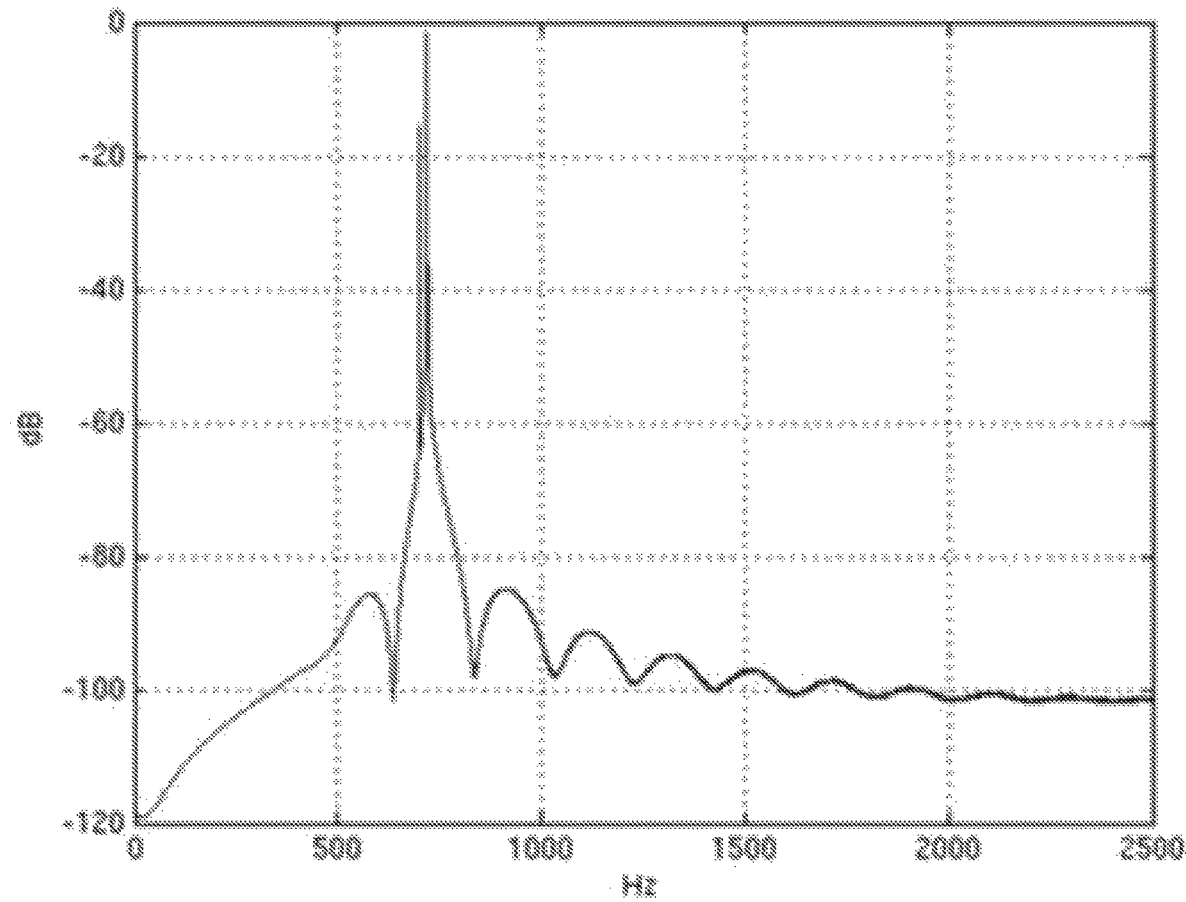
FIG. 9 is a simulated spectrum diagram of an example echo signal modulated by a human body, in accordance with embodiments of the present invention.

Referring now to FIG. 9, shown is a simulated spectrum diagram of an example echo signal modulated by a human body, in accordance with embodiments of the present invention. If the Doppler shift produced by human motion is 19.2 Hz, the respiratory frequency is 0.25 Hz, and the heart rate is 1.25 Hz. The frequency spectrum of the probe signal reflected by the human body is as shown in FIG. 9, whereby that energy of echo signal R(t) is basically concentrated around 700 Hz.

Figure 10:
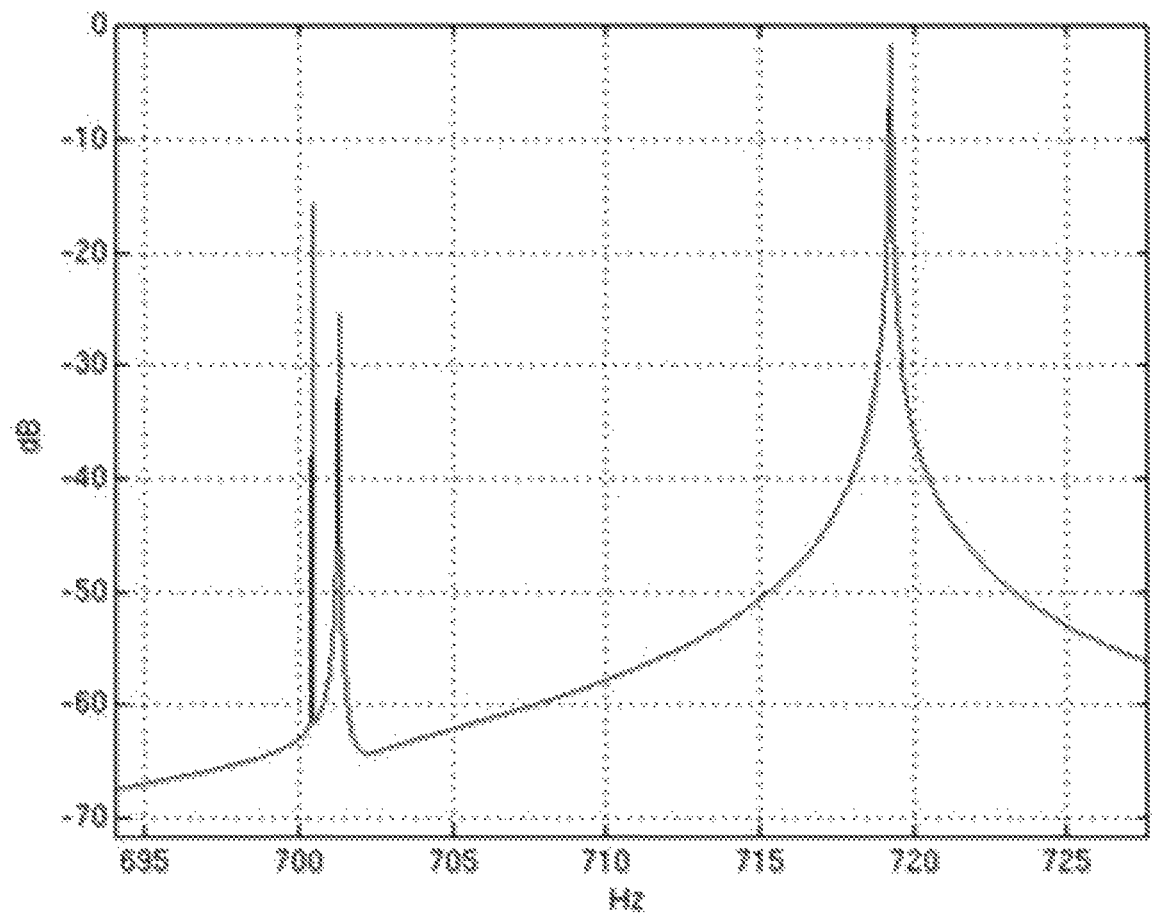
FIG. 10 is a simulated spectrum diagram of an example echo signal in a frequency band with relative large magnitude, in accordance with embodiments of the present invention.

Referring now to FIG. 10, shown is a simulated spectrum diagram of an example echo signal in a frequency band with relative large magnitude, in accordance with embodiments of the present invention. FIG. 10 is a spectrum diagram obtained by amplifying the spectrum diagram in FIG. 9 near 700 Hz, and shows that there are three peaks in the frequency spectrum of echo signal R(t), which are located between 700 Hz-705 Hz and near 720 Hz. The three peaks may correspond to the frequency shifts respectively caused by the respiratory frequency, heart rate, and movement.

Figure 11:
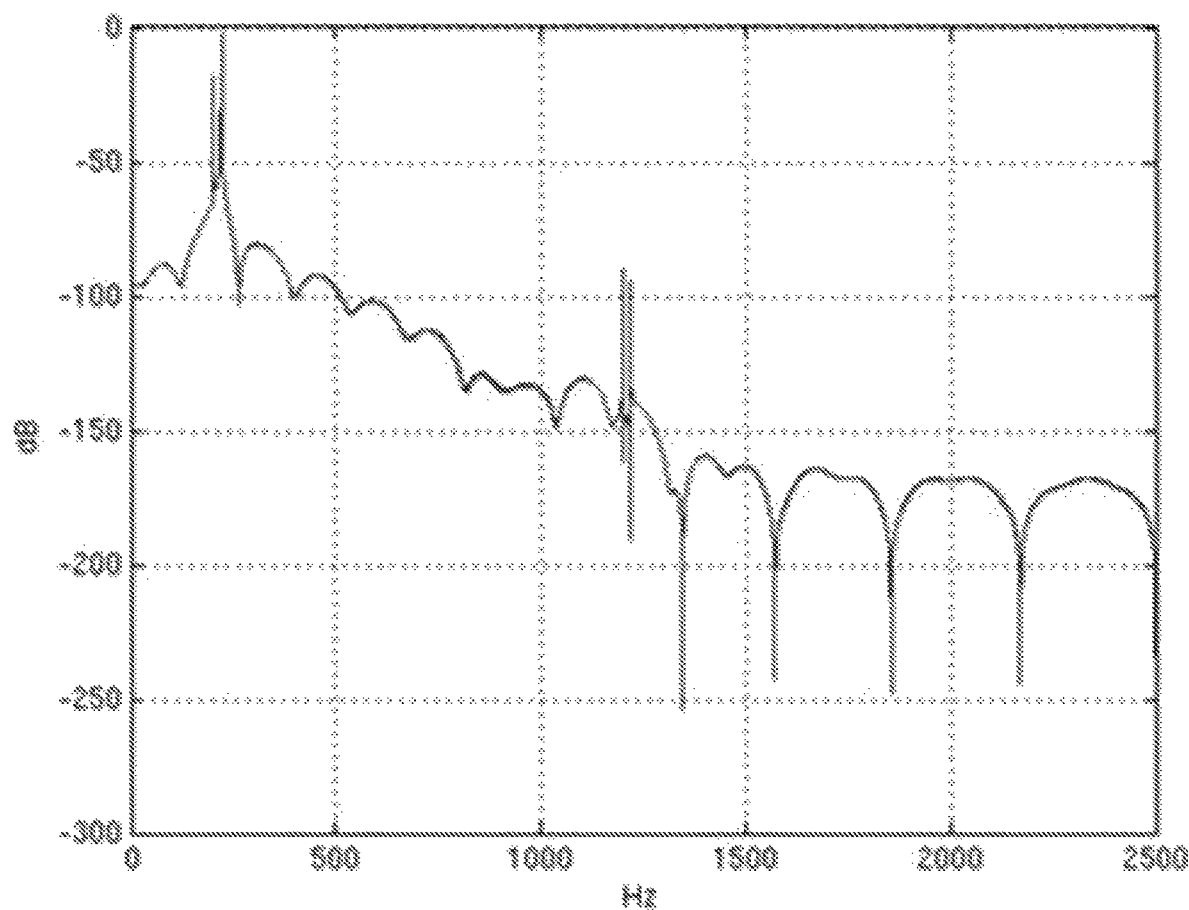
FIG. 11 is a simulated spectrum diagram of an example digital intermediate frequency receive signal obtained by down conversion, in accordance with embodiments of the present invention.

Referring now to FIG. 11, shown is a simulated spectrum diagram of an example digital intermediate frequency receive signal obtained by down conversion, in accordance with embodiments of the present invention. At the echo signal receiving terminal, the frequency spectrum of analog intermediate frequency receiving signal M(t) obtained by performing the first down conversion on echo signal R(t) is shown in FIG. 11, whereby the energy of analog intermediate frequency receiving signal M(t) is basically concentrated around 200 Hz.

Figure 12:
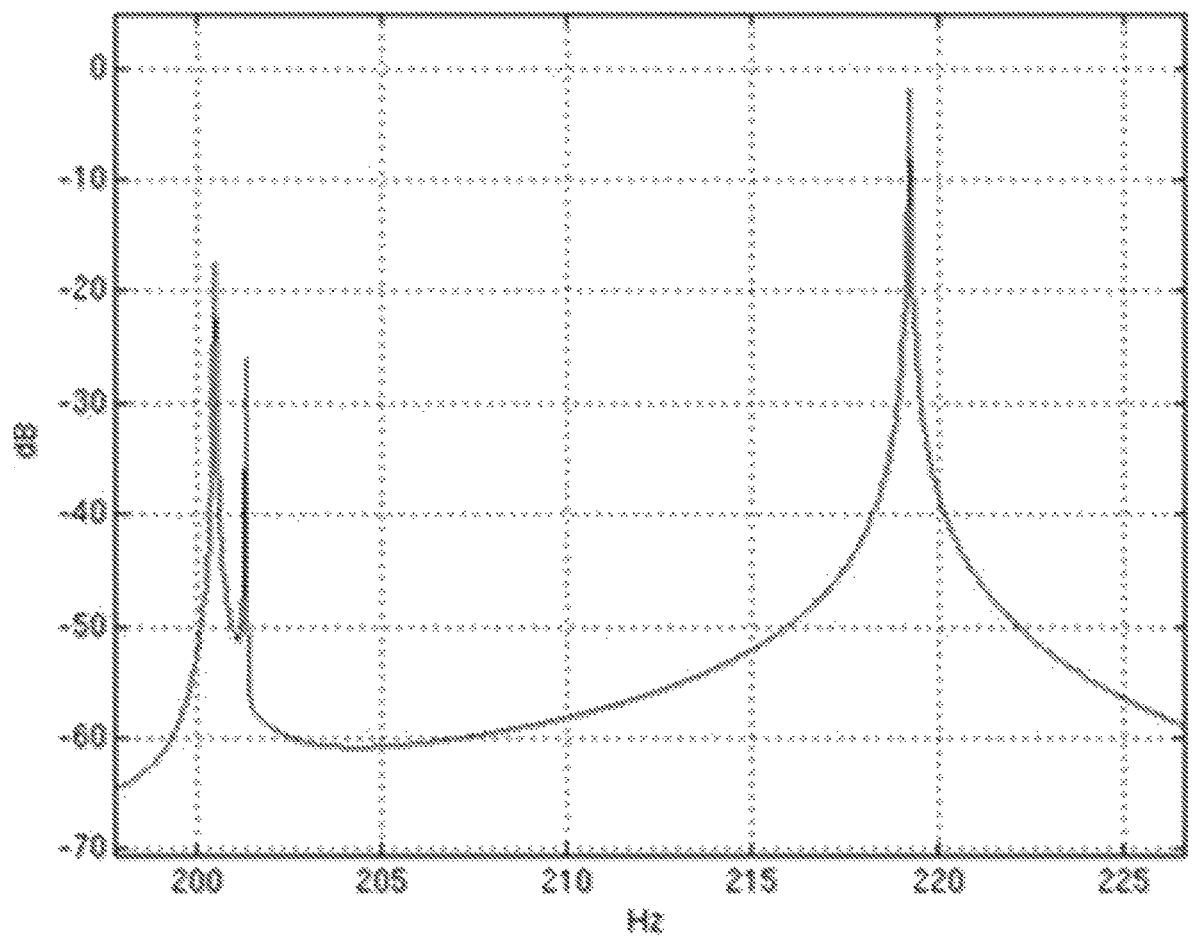
FIG. 12 is a simulated spectrum diagram of an example digital intermediate frequency receiving signal which is obtained by down conversion in a frequency band with relative large magnitude, in accordance with embodiments of the present invention.

Referring now to FIG. 12, shown is a simulated spectrum diagram of an example digital intermediate frequency receiving signal which is obtained by down conversion in a frequency band with relative large magnitude, in accordance with embodiments of the present invention. In this example, after amplifying the frequency spectrum near 200 Hz, it can be seen that there are three peaks in the energy of analog intermediate frequency receiving signal M(t), which are located between 200 Hz-205 Hz and near 220 Hz. The three peaks may correspond to the frequency shifts caused by the respiratory frequency, heart rate, and movement, respectively.

Figure 13:
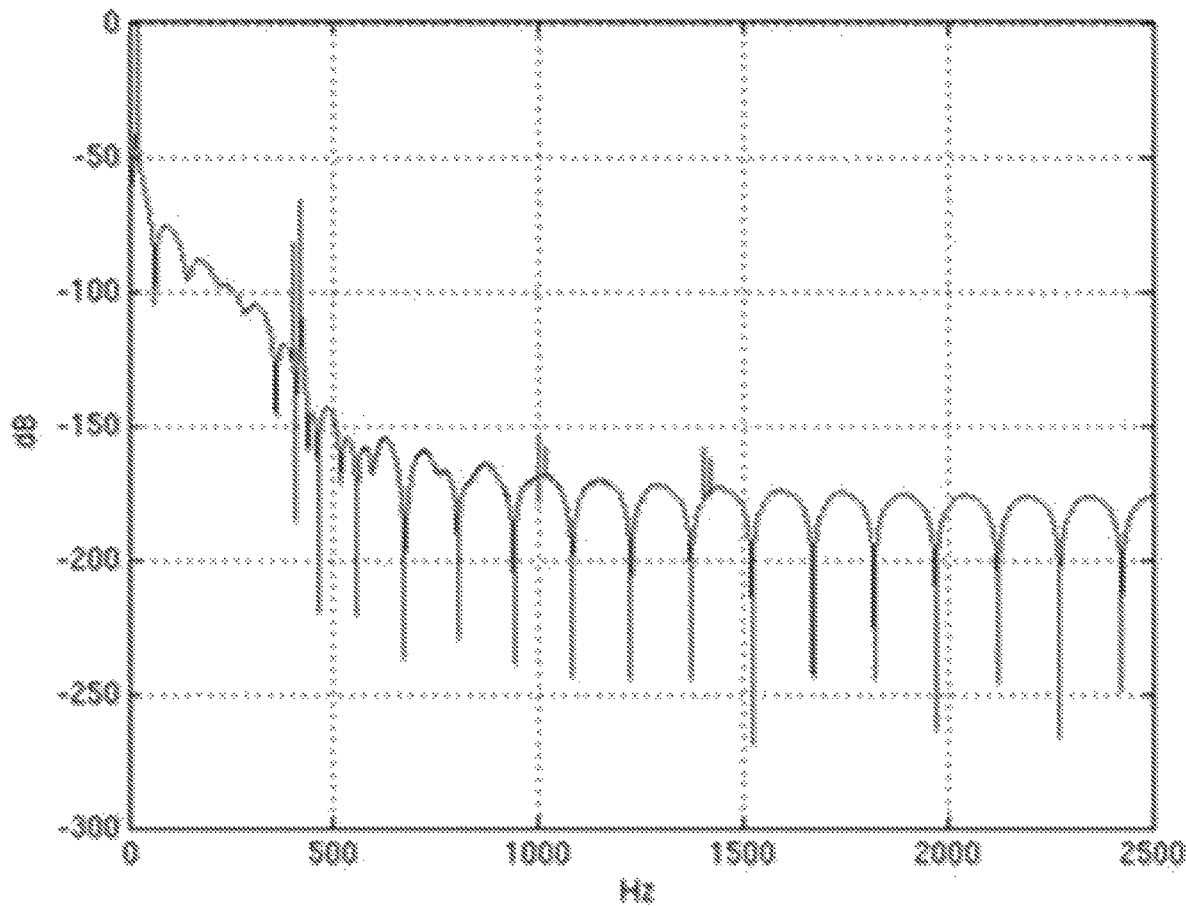
FIG. 13 is a simulated spectrum diagram of an example object feature signal obtained by second down conversion, in accordance with embodiments of the present invention.
Figure 14:
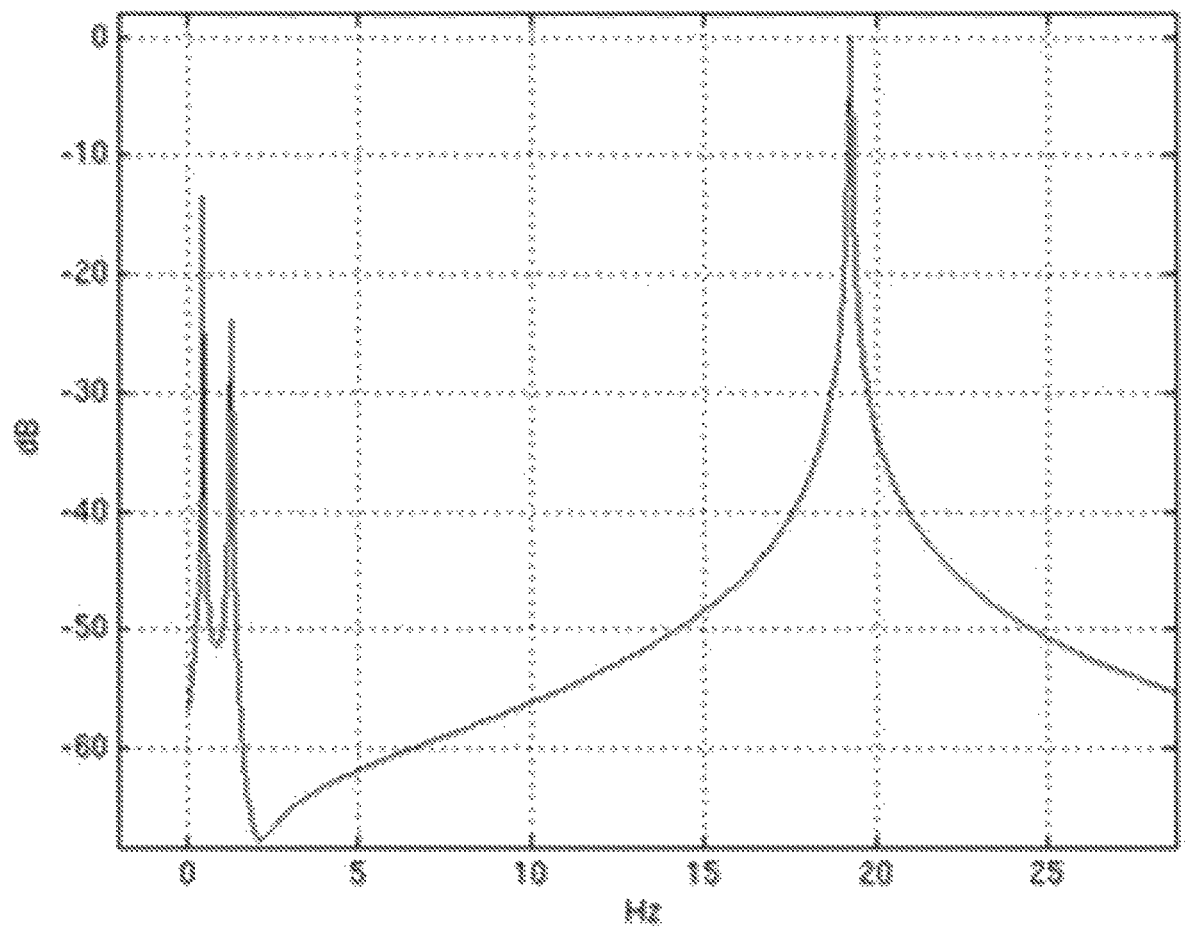
FIG. 14 is a simulated spectrum diagram of an example object feature signal obtained by second down conversion in a frequency band with relative large magnitude, in accordance with embodiments of the present invention.

Referring now to FIGS. 13 and 14, shown are simulated spectrum diagrams of an example object feature signal obtained by second down conversion, in accordance with embodiments of the present invention. At the echo signal receiving terminal, the analog intermediate frequency receiving signal M(t) can be further converted to digital intermediate frequency receiving signal M(n), and then converted to object feature signal B(n) through the second down conversion. The frequency spectrum of object feature signal B(n) and the amplified diagram of the frequency spectrum near 0 Hz are shown in FIGS. 13 and 14. As shown, there are three peaks in the energy of the object feature signal B(n) between 0-5 Hz and near 20 Hz, which may correspond to the frequency shifts caused by the respiratory frequency, heart rate, and movement.

At S300 in FIG. 3, as the sampling rate of the digital signal which is obtained through analog-to-digital conversion by the ADC is much higher than the frequency where the feature signal is concentrated, the object features can be detected by processing the object feature signal after the sampling rate of the object feature signal is reduced. The lower sampling rate can reduce the computation complexity of the data processing performed by signal processor 3, which is advantageous for the detection of the object features using signal processor 3 with lower specification, so as to reduce the product cost. In order to reduce the sampling rate, the object feature signal can be sampled and filtered before the object features are detected, and then the sampled and filtered object feature signal may be detected. For example, the sampling and filtering function can be realized by a decimation filter, such as a cascaded integrator-comb (CIC) filter.

Figure 15:
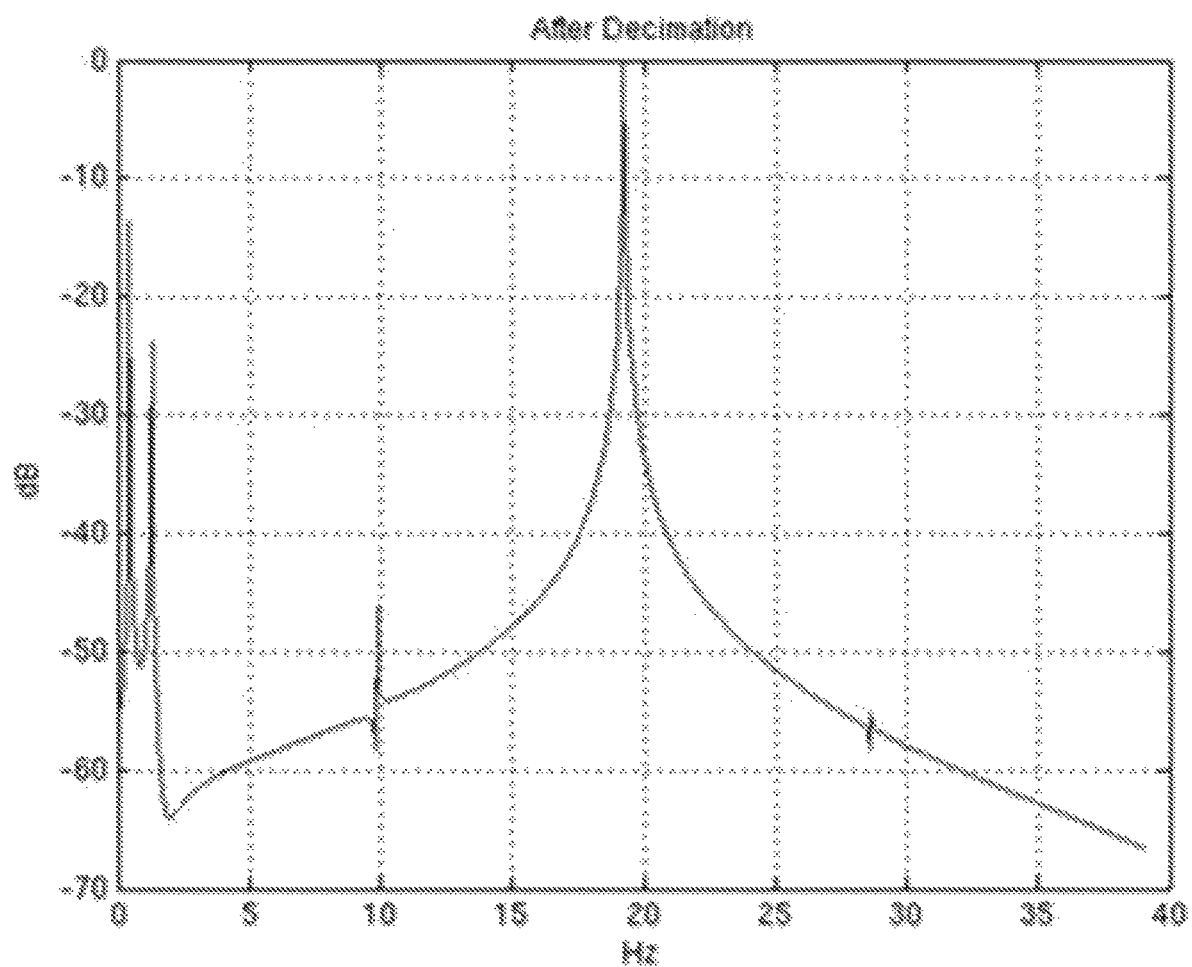
FIG. 15 is a simulated spectrum diagram of an example object feature signal obtained by decimate-filter, in accordance with embodiments of the present invention.

Referring now to FIG. 15, shown is a simulated spectrum diagram of an example object feature signal obtained by decimate-filter, in accordance with embodiments of the present invention. The frequency spectrum of the sampled and filtered object feature signal B(n) is shown in FIG. 15, whereby there is almost no change in the frequency spectrum before and after sampling and filtering, and therefore there may be no influence on the further detection of the object feature.

By loading a predetermined intermediate frequency signal onto a carrier signal of a predetermined frequency during transmission, by extracting the object feature signal in the reflected echo signal by two down-conversions when receiving the echo signal, and by introducing a digital intermediate frequency, negative influences of the low-frequency and direct-current interference signals on the detection of the object features can be substantially avoided. In addition, the accuracy of the detection can be improved, so as to further detect some of the weak features (e.g., respiration, heartbeat features, etc.).

In certain embodiments, the digital portions in probe signal transmitting terminal 1, echo signal receiving terminal 2, and signal processor 3 can be implemented with a field programmable logic array (FPGA), a digital signal processor (DSP), a high-performance programmable logic device (PLD), and/or an application specific integrated circuit (ASIC). The digital portions of these units can be separately implemented with the same type of device, or may be integrated in a unified device. Alternatively, these units can be separately implemented with different types of devices according to different requirements. For example, the above three digital portions may all be implemented in a DSP, or the digital portions of probe signal transmitting terminal 1 and echo signal receiving terminal 2 can be implemented in one device, while signal processor 3 is implemented in another device.

The embodiments were chosen and described in order to best explain the principles of the invention and its practical applications, to thereby enable others skilled in the art to best utilize the invention and various embodiments with modifications as are suited to particular use(s) contemplated. It is intended that the scope of the invention be defined by the claims appended hereto and their equivalents.

What is claimed is:

1. An apparatus for detecting object features, comprising:
   a) a probe signal transmitter configured to perform an up conversion by multiplying an analog intermediate frequency signal that is converted from a digital intermediate frequency signal and a carrier signal to generate a loaded signal, and to transmit said loaded signal outwards;
   b) an echo signal receiver configured to receive an echo signal, and to extract an object feature signal by multiplying said echo signal and a quadrature signal of said carrier signal to obtain an analog intermediate frequency receiving signal and converting said analog intermediate frequency receiving signal to a digital intermediate frequency receiving signal, and multiplying said digital intermediate frequency receiving signal and a quadrature signal of said digital intermediate frequency signal; and
   c) a signal processor configured to identify object features according to said object feature signal.

2. The apparatus of claim 1, wherein said probe signal transmitter comprises:
   a) a direct digital frequency synthesizer configured to generate said digital intermediate frequency signal;
   b) a digital-to-analog converter configured to convert said digital intermediate frequency signal to said analog intermediate frequency signal;
   c) a carrier wave generator configured to generate said carrier signal;
   d) a mixer configured to load said analog intermediate frequency signal onto said carrier signal; and
   e) a transmitting circuit configured to transmit a mixed signal.

3. The apparatus of claim 2, wherein said probe signal transmitter further comprises an anti-alias filter coupled between said direct digital frequency synthesizer and said digital-to-analog converter.

4. The apparatus of claim 2, wherein said probe signal transmitter further comprises a low-pass filter coupled between said digital-to-analog converter and said mixer.

5. The apparatus of claim 1, wherein said echo signal receiver comprises:
   a) a receiving circuit configured to receive said echo signal in a predetermined frequency band;
   b) a first down converter configured to perform down conversion on said received echo signal according to said quadrature signal of said carrier signal to obtain said analog intermediate frequency receiving signal;
   c) an analog-to-digital converter configured to convert said analog intermediate frequency receiving signal to said digital intermediate frequency receiving signal; and
   d) a second down converter configured to perform digital down conversion on said digital intermediate frequency receiving signal according to said quadrature signal of said digital intermediate frequency signal to extract said object feature signal.

6. The apparatus of claim 1, wherein said signal processor is configured to:
   a) perform sampling and filtering on said object feature signal; and
   b) obtain said object features according to said object feature signal that is obtained by sampling and filtering.

7. The apparatus of claim 1, wherein said object features comprise moving speed, respiratory frequency, and heart rate.

8. The apparatus of claim 7, wherein a first frequency band corresponds to a range of said moving speed, a second frequency band corresponds to a range of said respiratory frequency, and a third frequency band corresponds to a range of said heart rate.

9. The apparatus of claim 8, wherein said signal processor is configured to detect information of said object feature signal in said first, second, and third frequency bands, in order to obtain said moving speed, said respiratory frequency, and said heart rate of an object.

10. The apparatus of claim 8, wherein said signal processor is configured to detect whether a predetermined signal of said object feature signal exists in said first, second, and third frequency bands, in order to determine the presence of said object in a detection range.

11. A method of detecting object features, the method comprising:
    a) performing an up conversion by multiplying an analog intermediate frequency signal that is converted from a predetermined digital intermediate frequency signal and a carrier signal to generate a loaded signal, and transmitting said loaded signal outwards;
    b) receiving an echo signal in a predetermined receiving frequency band, and extracting an object feature signal by multiplying said echo signal and a quadrature signal of said carrier signal to obtain an analog intermediate frequency receiving signal and converting said analog intermediate frequency receiving signal to a digital intermediate frequency receiving signal, and multiplying said digital intermediate frequency signal and a quadrature signal of said digital intermediate frequency signal; and
    c) identifying object features according to said object feature signal.

12. The method of claim 11, further comprising:
    a) generating said digital intermediate frequency signal;
    b) converting said digital intermediate frequency signal to said analog intermediate frequency signal;
    c) generating said carrier signal;
    d) loading said analog intermediate frequency signal onto said carrier signal; and
    e) transmitting a mixed signal.

13. The method of claim 12, further comprising anti-alias filtering said digital intermediate frequency signal before digital-to-analog conversion is performed.

14. The method of claim 12, further comprising low-pass filtering said analog intermediate frequency signal before frequency mixing.

15. The method of claim 11, further comprising:
    a) receiving said echo signal in said predetermined receiving frequency band;
    b) performing down conversion on said received echo signal according to said quadrature signal of said carrier signal, and obtaining said analog intermediate frequency signal;
    c) converting said analog intermediate frequency receiving signal to said digital intermediate frequency receiving signal; and
    d) performing digital down conversion on said digital intermediate frequency receiving signal according to said quadrature signal of said digital intermediate frequency signal to extract said object feature signal.

16. The method of claim 11, further comprising:
    a) performing decimation filtering on said object feature signal; and b) obtaining said object features according to said object feature signal that is obtained by said decimation filtering.

17. The method of claim 11, wherein said object features comprise moving speed, respiratory frequency, and heart rate.

18. The method of claim 17, wherein a first frequency band corresponds to a range of said moving speed, a second frequency band corresponds to a range of said respiratory frequency, and a third frequency band corresponds to a range of said heart rate.

19. The method of claim 18, further comprising detecting information of said object feature signal in said first, second, and third frequency bands to obtain said moving speed, said respiratory frequency, and said heart rate of an object.

20. The method of claim 18, further comprising detecting whether a predetermined signal of said object feature signal exists in said first, second, and third frequency bands, in order to determine the presence of said object in a detection range.

\* \* \* \* \*